(12) United States Patent
George

(10) Patent No.: US 9,445,636 B2
(45) Date of Patent: Sep. 20, 2016

(54) EASILY REMOVABLE MEDICAL GLOVES

(71) Applicant: Ashwin George, Eagan, MN (US)

(72) Inventor: Ashwin George, Eagan, MN (US)

( * ) Notice: Subject to any disclaimer, the term of this patent is extended or adjusted under 35 U.S.C. 154(b) by 0 days.

(21) Appl. No.: 14/833,457

(22) Filed: Aug. 24, 2015

(65) Prior Publication Data

US 2015/0359276 A1 Dec. 17, 2015

Related U.S. Application Data

(63) Continuation of application No. 13/468,528, filed on May 10, 2012, now Pat. No. 9,113,666.

(51) Int. Cl.
*A41D 19/015* (2006.01)
*A41D 19/00* (2006.01)

(52) U.S. Cl.
CPC ....... *A41D 19/0044* (2013.01); *A41D 19/0062* (2013.01); *A41D 19/015* (2013.01); *A41D 19/0058* (2013.01); *A41D 2400/70* (2013.01); *A61B 42/00* (2016.02)

(58) Field of Classification Search
CPC ........... A41D 19/015; A41D 19/0044; A41D 19/0058; A41D 2400/70
USPC ............. 2/16, 20, 161.7, 162, 167, 168, 170
See application file for complete search history.

(56) References Cited

U.S. PATENT DOCUMENTS

| | | | |
|---|---|---|---|
| 1,687,380 A | 10/1928 | Meyers | |
| 4,070,713 A | 1/1978 | Stockum | |
| 4,464,796 A | 8/1984 | Heissenberger et al. | |
| 4,845,781 A * | 7/1989 | Strickland | A61B 19/04 2/161.6 |
| 4,876,747 A | 10/1989 | Coffey et al. | |
| 5,020,160 A | 6/1991 | Cano | |
| 5,365,608 A | 11/1994 | Flick | |
| 5,467,483 A | 11/1995 | Saadatmanesh et al. | |
| 5,579,539 A | 12/1996 | Flick | |
| 5,867,832 A | 2/1999 | Liu | |
| 6,029,277 A | 2/2000 | Picchione, II | |
| 6,393,614 B1 | 5/2002 | Eichelbaum | |
| 7,665,150 B2 | 2/2010 | Holley | |
| 7,761,931 B2 * | 7/2010 | Schrodl | A41D 19/0082 2/161.1 |
| 7,908,673 B2 | 3/2011 | Kerr-Maddox et al. | |
| 8,015,622 B1 | 9/2011 | Bhalla | |
| 9,113,666 B2 * | 8/2015 | George | A41D 19/015 |
| 2005/0229287 A1 | 10/2005 | Mattesky | |
| 2009/0077701 A1 * | 3/2009 | Holley | A41D 19/0044 2/16 |
| 2012/0124711 A1 | 5/2012 | Tuttle | |

* cited by examiner

*Primary Examiner* — Katherine Moran
(74) *Attorney, Agent, or Firm* — Vidas, Arrett & Steinkraus, P.A.

(57) ABSTRACT

A glove sized and shaped to enclose a human hand, the medical glove having a two-layer cuff, the two layers being fixed to one another at a plurality of locations to define a plurality of spaced apart openings in the cuff, the openings accessible only outside the glove.

4 Claims, 4 Drawing Sheets

EASILY REMOVABLE MEDICAL GLOVES

CROSS-REFERENCE TO RELATED APPLICATIONS

This application is a continuation of U.S. patent application Ser. No. 13/468528 filed May 10, 2012, the entire content of which is hereby incorporated by reference.

STATEMENT REGARDING FEDERALLY SPONSORED RESEARCH

Not Applicable

BACKGROUND OF THE INVENTION

To prevent the spread of disease or contamination, health care professionals wear gloves on their hands when treating patients. During use, the outside of the gloves becomes contaminated. The health care professional needs to take care in removing the gloves from their hands in order to avoid contaminating the skin being protected by the gloves.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In at least one embodiment, a medical glove sized to fit a wearer's hand is made of glove material and has a closed end, an open end, an outer surface, an inner surface, a glove body, and a cuff. The glove body is made of one layer of glove material. The cuff is made of two layers of glove material. The two layers of glove material forming the cuff are attached to one another at a plurality of attachment locations separated one from another about the perimeter of the cuff.

These and other embodiments which characterize the invention are pointed out with particularity in the claims annexed hereto and forming a part hereof. However, for further understanding of the invention reference can be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
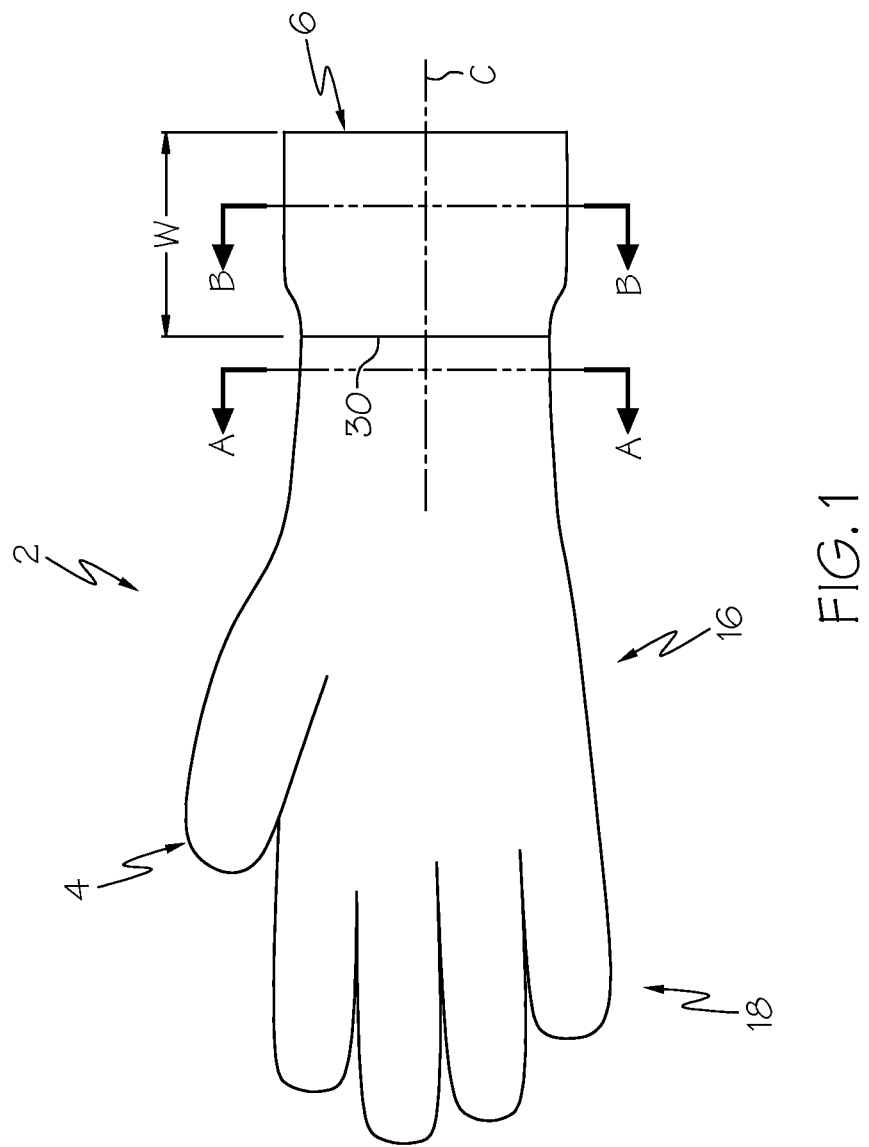
FIG. 1 is a view of a glove.
Figure 2:
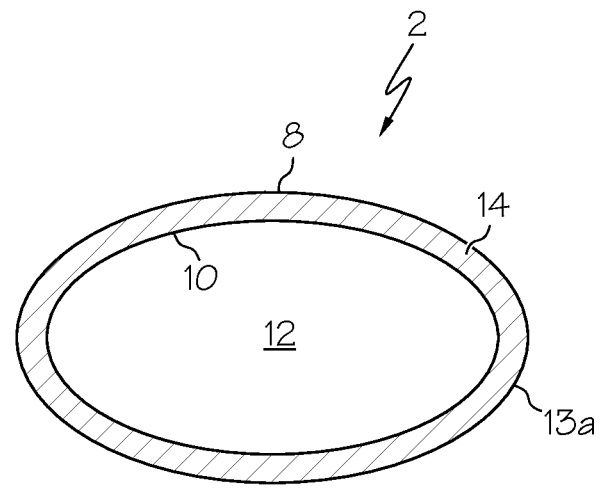
FIG. 2 is a cross-sectional view of the glove of FIG. 1 at line A-A.

While the glove disclosed herein may be embodied in many different forms, there are described in detail herein specific embodiments of the glove. This description is an exemplification of the principles of the glove and is not intended to limit the glove to the particular embodiments illustrated.

For the purposes of this disclosure, like reference numerals in the figures shall refer to like features unless otherwise indicated, and the reference numerals indicate elements shown in the figures.

As used in this application, "wearer" refers to a human. As used in this application, a "hand" is the terminal part of the human arm located below the forearm consisting of the wrist, palm, four fingers, and an opposable thumb.

The term "width," as used herein in reference to any element of the glove 2 or a wearer, is measured in the direction extending from the open end 6 to the closed end 4 of the glove 2 (see e.g. width W in FIG. 1); "perimeter length" or "length" as used herein in reference to any element of the glove 2 or a wearer is measured in the direction extending around the glove 2 (see e.g. length "P" in FIG. 3 and length "L" in FIG. 6).

A glove 2 as shown in the figures can be used for medical purposes, such as examination or surgery, or for non-medical purposes, such as in the laboratory, and elsewhere. Hereinafter the glove 2 is referred to as a medical glove. In at least one embodiment, the medical glove 2 is sized to fit a wearer's hand. The medical glove 2 has a closed end 4, an open end 6, an outer surface 8, and an inner surface 10. The open end 6 of the medical glove 2 provides an entry point for the wearer's hand. Thus the inner surface 10 defines a cavity 12 that is sized for the wearer's hand. The medical glove 2 can be right handed, left handed, or ambidextrous. The medical glove 2 can be considered to have two "sides" with one side being adjacent to a palm of the wearer's hand (hereinafter the palm side) and the other side being adjacent to the back of the wearer's hand (hereinafter the back side).

The medical glove 2 is formed of glove material 14 and includes a glove body 16 and a cuff 20. In some embodiments, the glove body 16 is made of one layer 13a of glove material 14. The glove body 16 includes five fingers 18 at the closed end 4 of the medical glove 2. The five fingers 18 enclose the four fingers and thumb of the wearer's hand. In some embodiments, when the medical glove 2 is worn by the wearer, the glove body 16 encloses the wearer's hand. In other embodiments, when the medical glove 2 is worn by the wearer, the glove body 16 encloses the wearer's hand and at least a portion of the wearer's forearm adjacent to the hand.

The cuff 20 forms, and extends from, the open end 6 of the medical glove 2. In at least one embodiment, the cuff 20 extends from the glove body 16. In some embodiments, when the medical glove 2 is being worn, the cuff 20 encloses at least a portion of the wearer's wrist. As shown in FIGS.

1 and 3, the cuff 20 has a width (W) and a perimeter length (P) that extends about the entire perimeter of the cuff 20. The width (W) of the cuff 20 is from 0.4 inches to 0.6 inches, or from 1.0 cm to 1.5 cm. In at least one embodiment, the width (W) of the cuff 20 is less than the width of the wearer's wrist. The cuff 20 can be described as being positioned a distance away from the wearer's hand. In some embodiments, the cuff 20 covers a portion of the forearm when the medical glove 2 is worn by the wearer. The perimeter length (P) of the medical glove 2 at the cuff 20 is sized for the wearer's wrist and/or forearm.

Figure 3:
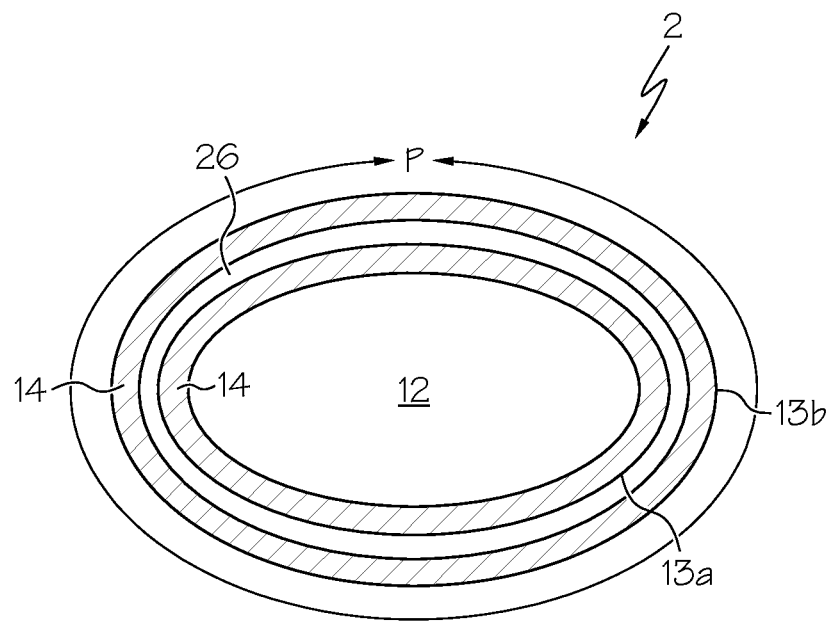
FIG. 3 is a cross-sectional view of a portion of the glove of FIG. 1 at line B-B. For simplicity, the attachment locations of the glove have been omitted from FIG. 3.
Figure 4:
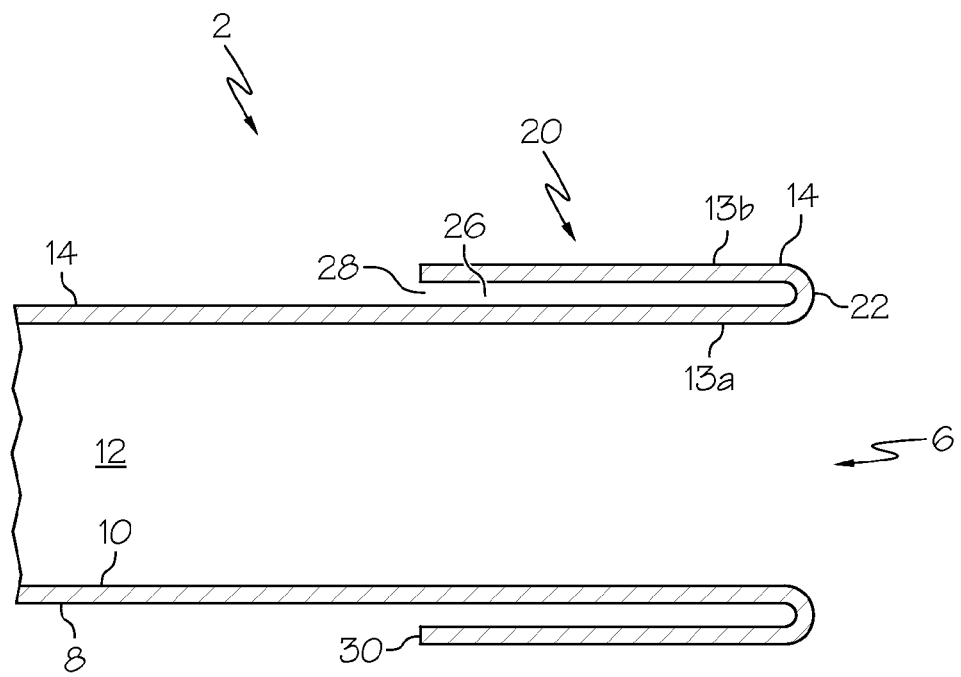
FIG. 4 is a cross-sectional view of a portion of the glove of FIG. 1 at line C-C. For simplicity, the attachment locations of the glove have been omitted from FIG. 4.
Figure 5:
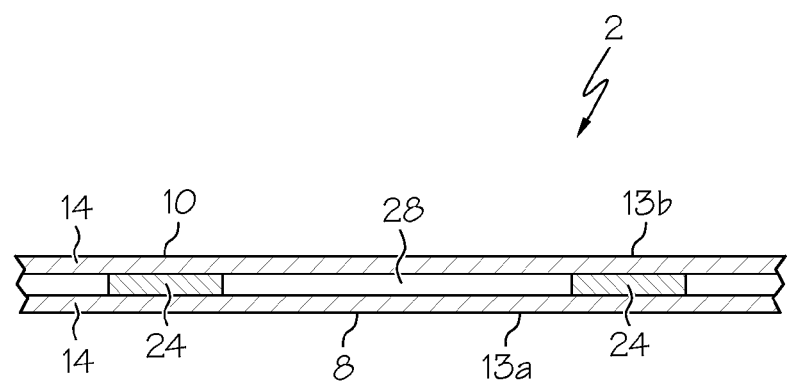
FIG. 5 is an end view of the bottom portion of the glove of FIG. 4.

As shown in FIGS. 3-5, the cuff 20 is made of two layers 13a,b of glove material 14, and has a first end 22 and a second end 30. As shown in the figures, the second 30 of the cuff 20 has a substantially straight configuration. However, the second end 30 can have other configurations, e.g. wavy, or zig-zagged, or any other suitable configuration.

The glove material 14 can be considered as comprising a first section that forms the glove body 16 and a portion of the cuff 20, and a second section that forms another portion of the cuff 20. The layers 13a,b of glove material 14 forming the cuff 20 are adjacent to one another. The layers 13a,b of glove material 14 forming the cuff 20 can be considered to be radially adjacent to one another relative to the cavity 12 of the medical glove 2. The inner surface 10 of the medical glove 2 is formed by the layer 13a of glove material 14 forming the glove body 16 and by the first layer 13a of glove material 14 forming the cuff 20. The outer surface 8 of the medical glove 2 is formed by the layer 13a of glove material 14 forming the glove body 16 and by the second layer 13b of glove material 14 forming the cuff 20.

In at least one embodiment, the first end 22 of the cuff 20 is a fold 22. As shown in the figures, the fold 22 is a portion of the layer 13 of glove material 14 that is bent over on itself (folded). In this embodiment, the fold 22 defines the open end 6 of the medical glove 2. The fold 22 can also be considered as forming a closed end of the cuff 20.

Figure 6:
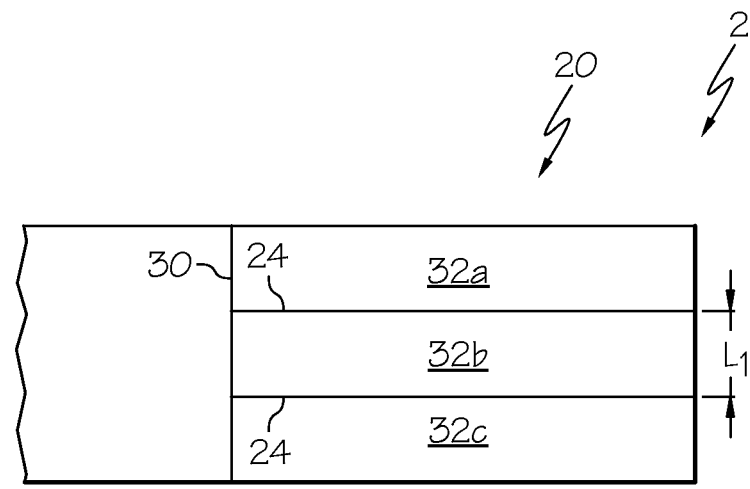
FIGS. 6-7 are views of a portion of the glove of FIG. 1 showing exemplary attachment locations for the cuff.
Figure 7:
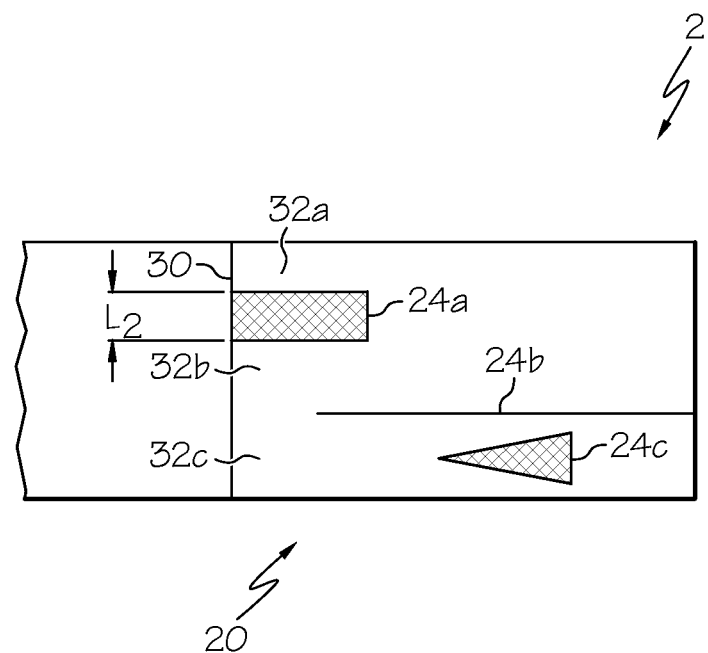

As shown in FIGS. 5-7, the two layers 13a,b of glove material 14 forming the cuff 20 are attached to one another at a plurality of locations 24 about the perimeter of the cuff 20. In some embodiments, the thickness of the cuff 20 is uniform. For example, as shown in FIG. 5, the thickness of the cuff 20 between the attachment locations 24 and at the attachment locations 24 is substantially the same. The cuff 20 shown in FIG. 5 can also be described as having a uniform, or a smooth or flat, exterior surface. In other embodiments, the thickness of the cuff 20 is non-uniform. For example, the thickness of the cuff 20 at the attachments locations 24 is less than the thickness of the cuff 20 between the attachment locations 24 (not shown). In this embodiment the exterior surface of the cuff 20 can be described as having a non-uniform, or an irregular or corrugated, surface.

In at least one embodiment, the locations 24 are offset from the open end of the medical glove 2. The locations 24 can also be described as being offset from the fold 22, or as being offset from the closed end of the cuff 20. As shown for example in FIG. 6, the locations 24 extend from the fold 22 and thus at least a portion of the location is offset from the fold 22. The two layers 13a,b of glove material 14 forming the cuff 20 can be attached to one another by any suitable means, including but not limited to, adhesive, heat bonding, stitching, hook and loop fasteners such as Velcro®, and combinations thereof Thus these locations 24 can be considered as "securement locations" or "attachment locations." Hereinafter, attachment location will be used. As used in this application, the fold 22 is not considered to be an attachment location 24. The securement of the two layers of glove material to one another at an attachment location is optimally semi-permanent or permanent.

In some embodiments, the cuff 20 has two, three, four, five, or six attachment locations 24. In one embodiment, the cuff 20 has a minimum of four attachment locations. In some embodiments, the attachment locations 24 extend parallel to a long axis (not shown) of the cuff 2. This is shown for example in FIG. 6. In other embodiments, the attachment locations do not extend parallel to the long axis of the cuff (not shown). In some embodiments, the attachment locations 24 are parallel to one another. This is shown for example in FIG. 6. In other embodiments, the attachment locations 24 are not parallel to one another (not shown). In at least one embodiment, at least a portion of the attachment location 24 is offset from the fold 22. This is shown, for example, by the attachment locations 24 of FIGS. 6 and 7.

Each attachment location 24 has a width and a length sufficient to attach the two layers of glove material 14 forming the cuff 20 to one another. The width of the attachment location is at most equal to the width (W) of the cuff 20, as shown, for example, in FIG. 6. In some embodiments, the width of the attachment location 24 is equal to the width of the cuff 20. This is shown for example in FIG. 6. The attachment locations 24 in FIG. 6 can also be described as extending from the fold 22 or closed end of the cuff 20 or open end 6 of the medical glove 2 to the open end 30 of the cuff 20. In other embodiments, the width of the attachment location 24 is less than the width (W) of the cuff 20. Non-limiting examples of attachment locations 24a, 24c having a width less than the width of the cuff are provided in FIG. 7. The length (L2) of the attachment location 24 is less than the perimeter length (P) of the cuff 20. In some embodiments, the length of the attachment location is uniform. This is shown for example by the attachment locations 24 in FIG. 6 and by location 24a in FIG. 7. In other embodiments, the length of the attachment location 24 is non-uniform. This is shown for example by location 24c in FIG. 7. In some embodiments, the length of the attachment location is from 0.40 inches to 3 inches, or from 1.0 cm to 7.62 cm.

Each attachment location 24 has a configuration based on the characteristics of the width and length of the attachment location 24. In some embodiments, each attachment location 24 of a medical glove 2 has the same configuration. For example, as shown in FIG. 6, the attachment locations 24a, 24b have the same configuration. In other embodiments, the attachment locations 24 of a medical glove 2 have different configurations. For example, as shown in FIG. 7, the attachment locations 24a, 24b, 24c have different configurations from one another.

The attachment locations 24 are separated one from another by a length (L1) and adjacent locations define an opening 28 in the cuff 20 which leads to the space 26 between the two layers of glove material 14 forming the cuff 20. The opening 28, shown by way of example in FIG. 4, is adjacent to, and only accessible from, the outer surface 8 of the medical glove 2.

In at least one embodiment, the length (L1) between two adjacent attachment locations 24, and thus the length of the opening 28, is sized to receive a human finger. In at least one embodiment, the attachment locations 24 are equidistant from one another about the perimeter of the cuff 20. In some embodiments, two attachment locations 24 are located on the palm side of the medical glove 2 and two attachment locations 24 are located on the back side of the medical glove 2. In one embodiment, one opening 28 is located on the palm side of the medical glove 2 and one opening 28 is located on the back side of the medical glove 2. In some embodiments, the length (L1) between two adjacent attachment locations 24 is from 0.40 inches to 0.80 inches, or from 1.0 cm to 2.0 cm. Thus, in these embodiments, the opening 28 has a length from 0.40 inches to 0.80 inches, or from 1.0 cm to 2.0 cm. In other embodiments, the length (L1) between two attachment locations 24 is equal to one quarter of the perimeter length (P) of the cuff 20. In still other embodiments, the length (L1) between two attachment locations is equal to one fifth of the perimeter length (P) of the cuff 20.

The cuff 20 can also be described as having a plurality of first portions 24 where the two layers 13*a,b* of material 14 forming the cuff 20 are attached to one another; and a plurality of second portions 32*a*, 32*b*, and 32*c* where the two layers 13*a,b* of material 14 forming the cuff 20 are separated from one another and define an opening 28 accessible from outside the glove body 16. The cuff 20 can also be described as having a plurality of closed regions 24 and a plurality of open regions 28 with each open region 32*a*, 32*b*, and 32*c* being between two closed regions 24. In some embodiments, the second portion or open region has three closed sides and one open side that forms a portion of the second end 30 of the cuff 20; and the first portion or closed region 24 has four closed sides.

In at least one embodiment, the wearer can remove the medical glove 2 by inserting a finger into an opening 28 of the cuff 20 and using the finger to move the cuff 20 towards the wearer's fingers 18. In one embodiment, this method of removal prevents contamination of the wearer's wrist as the medical glove 2 is being removed.

In some embodiments, a medical glove 2 is made by providing a glove made of a layer 13*a* of material 14 defining an open end; folding the layer 13*a* of glove material 14 at the open end to form a cuff 20 with a fold 22, where the fold 22 defines the open end 6 of the medical glove 2 and the cuff has two layers 13*a,b* of glove material 14; securing the two layers 13*a,b* of glove material 14 of the cuff 20 to one another at a plurality of attachment locations 24. In some embodiments, the method further comprises applying heat to the fold 22. This can help set the fold 22. The two layers 13*a,b* of glove material 14 may be secured by any suitable method, including but not limited to, an adhesive, heat bonding, stitching, and combinations thereof.

In other embodiments, a medical glove 2 is made by forming a glove made of a layer 13*a* of glove material 14 defining an open end; folding the layer 13*a* of glove material 14 at the open end to form a cuff 20 with a fold 22, where the fold 22 defines the open end 6 of the medical glove 2 and the cuff 20 has two layers 13*a,b* of glove material 14; securing the two layers 13*a,b* of glove material 14 of the cuff 20 to one another at a plurality of attachment locations 24. In some embodiments, the method further comprises applying heat to the fold 22. This can help set the fold 22. The two layers 13*a,b* of glove material 14 may be secured by any suitable method, including but not limited to, an adhesive, heat bonding, stitching, hook and loop fasteners such as Velcro®, and combinations thereof. The securement of the two layers of glove material to one another at an attachment location is optimally semi-permanent or permanent.

In at least one embodiment, the glove material 14 is an elastomeric material. Materials suitable for the glove material 14 include, but are not limited to, latex, rubber, nitrile, neoprene, vinyl, and combinations thereof.

In at least one embodiment, at least one of the surface 8, 10 of the medical glove 2 includes an optional surface treatment, such as coating or finish. In some embodiments, the inner surface 10 has an optional surface treatment and the outer surface 8 has no surface treatment. In other embodiments, the inner and outer surfaces 8, 10 each have an optional surface treatment. In one embodiment, the optional surface treatment is the same for the inner surface 10 and the outer surface 8. In another embodiment, the inner surface 10 has a different optional surface treatment than the outer surface 8. In at least one embodiment, the surface treatment is optionally a coating or layer of powder. Examples of a powder includes, but not limited to, modified cornstarch or calcium carbonate.

In some embodiments, the medical glove 2 is sterile. In other embodiments, the medical glove 2 is not sterile. In at least one embodiment, the medical glove 2 is disposable. In some embodiments, the medical glove 2 is reusable.

Medical gloves that are also within the scope of the invention are described below:

1. A medical glove made of a glove material, the medical glove having an open end and a closed end, the medical glove comprising:
    a glove body sized and shaped to enclose a human hand; and
    a cuff extending from the glove body;
    a first section of the glove material forming the glove body and a first portion of the cuff;
    a second section of the glove material forming a second portion of the cuff;
    the first and second sections of glove material defining a fold in the glove at the open end of the glove;
    the second section and the first section secured to one another at a plurality of attachment locations other than at the fold;
    the glove body and the second portion of the cuff forming an outer surface of the medical glove and the glove body and the first portion of the cuff forming an inner surface of the medical glove.
2. The medical glove of statement 1, the plurality of attachment locations being at least four attachment locations.
3. The medical glove of statement 2, the four attachment locations being equidistant from one another.
4. The medical glove of statements 2-3, the medical glove having two sides, each side of the medical glove having two of the at least four attachment locations.
5. The medical glove of statement 4, the two attachment locations on a side of the medical glove being separated by a length equal to one fifth to one quarter of a perimeter of the cuff.
6. The medical glove of statements 1-5, the inner surface of the medical glove having a surface treatment, the outer surface having no surface treatment.
7. The medical glove of statements 1-6, each attachment location having a width at most equal to a width of the second section of the glove material and a length less than a perimeter length of the cuff.
8. The medical glove of statement 7, the length of each attachment location being equal to one eighth of the perimeter of the cuff.
9. The medical glove of statement 7, the length of each attachment location being equal to one sixth of the perimeter of the cuff.
10. The medical glove of statements 1-9, wherein the second section of the glove material has a length between 0.4 inch and 0.60 inch.
11. A medical glove, the medical glove comprising a glove body sized and shaped to enclose a human hand, the glove body made of a glove material and having an open end to receive a human hand, the open end defined by a fold of the glove material, the glove comprising:

a hand portion, the hand portion being one layer of the glove material, and a cuff portion extending from the hand portion to an end of the glove body, the cuff portion being two layers of the glove material, the cuff portion comprising:
- a first end, the first end of the cuff portion forming the open end of the glove body;
- a second end;
- a width extending from the first end of the cuff portion to the second end of the cuff portion;
- a plurality of first portions where the two layers of glove material are joined one to the other at a region other than the fold, the region extending at least a part of the width of the cuff portion; and
- a plurality of second portions where the two layers of glove material are separated from one another, the second portions having openings which are accessible from outside the glove body.

12. The medical glove of statement 11, having a palm side and back side opposite the palm side, the palm side and the back side connected one to the other along a first side and along a second side,
wherein the palm side and the back side each have at least one first portion disposed between the first side and the second side 13. The medical glove of statements 11-12, wherein the length of the second portions is greater than the length of the first portions.

14. The medical glove of statements 11-13, wherein the width of the cuff is from 0.4 inches to 0.6 inches.

15. The medical glove of statements 11-14, each second portion having a maximum length of 2 cm (0.78 inches).

16. A medical glove,
the medical glove having an open end, a closed end, a front side, a back side,
the medical glove including a cuff terminating at the open end of the medical glove, the cuff having an open end and a closed end, the closed end located at the open end of the medical glove,
the cuff having two layers, the two layers secured to one another at a minimum of four securement locations and defining open spaces between the securement locations, at least a portion of the securement locations offset from the closed end of the cuff, the open spaces accessible only from the outside of the glove.

17. The medical glove of statement 16 wherein there are at least two securement locations on the front side of the medical glove and at least two securement locations on the back side of the medical glove.

18. The medical glove of statement 17 wherein:
securement regions which are adjacent one another on the front side of the medical glove are spaced apart sufficiently to form a channel in the cuff sized to receive a human finger therein; and
securement regions which are adjacent one another on the back side of the medical glove are spaced apart sufficiently to form a channel in the cuff sized to receive a human finger therein.

19. The medical glove of statements 17-18 wherein:
securement regions which are adjacent one another on the front side of the glove are spaced apart by at least one centimeter; and securement regions which are adjacent one another on the back side of the glove are spaced apart sufficiently by at least one centimeter.

20. A medical glove sized and shaped to enclose a human hand, the medical glove having a two-layer cuff, the two layers being fixed to one another at a plurality of locations to define a plurality of spaced apart openings in the cuff, the openings accessible only outside the glove.

21. The medical glove of claim 20 having a palm side and a back side opposite the palm side, and plurality of spaced apart openings in the cuff on the back side and a plurality of spaced apart openings in the cuff on the palm side.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A medical glove,
the medical glove having an open end, a closed end, a front side, a back side, a portion of the medical glove for enclosing a hand portion and being formed of a single layer,
the medical glove including a cuff terminating at the open end of the medical glove, the cuff having an open end and a closed end, the closed end located at the open end of the medical glove,
the cuff having two layers, the two layers secured to one another at a minimum of four securement locations and defining open spaces between the securement locations, at least a portion of the securement locations offset from the closed end of the cuff, the open spaces accessible only from the outside of the glove.

2. The medical glove of claim 1 wherein there are at least two securement locations on the front side of the medical glove and at least two securement locations on the back side of the medical glove.

3. The medical glove of claim 2 wherein:
securement locations which are adjacent one another on the front side of the medical glove are spaced apart sufficiently to form a channel in the cuff sized to receive a human finger therein; and
securement locations which are adjacent one another on the back side of the medical glove are spaced apart sufficiently to form a channel in the cuff sized to receive a human finger therein.

4. The medical glove of claim 2 wherein:
securement locations which are adjacent one another on the front side of the glove are spaced apart by at least one centimeter; and
securement locations which are adjacent one another on the back side of the glove are spaced apart sufficiently by at least one centimeter.

* * * * *